United States Patent [19]

Riddell

[11] Patent Number: 4,820,269

[45] Date of Patent: * Apr. 11, 1989

[54] MIXER APPARATUS FOR CONTROLLING INTRAVENOUS DRUG INFUSION

[75] Inventor: James G. Riddell, Belfast, Ireland

[73] Assignee: Vanderbilt University, Nashville, Tenn.

[ * ] Notice: The portion of the term of this patent subsequent to Nov. 18, 2003 has been disclaimed.

[21] Appl. No.: 927,810

[22] Filed: Nov. 6, 1986

Related U.S. Application Data

[63] Continuation-in-part of Ser. No. 723,215, Apr. 15, 1985, Pat. No. 4,623,334, which is a continuation-in-part of Ser. No. 472,926, Mar. 7, 1983, abandoned.

[51] Int. Cl.$^4$ .............................................. A61M 5/00
[52] U.S. Cl. ..................... 604/85; 137/268; 604/92
[58] Field of Search ............ 604/56, 128, 82–86, 604/92, 246, 257, 411, 414, 251, 29; 366/131, 341; 222/190; 137/896–897, 268

[56] References Cited

U.S. PATENT DOCUMENTS

| | | | |
|---|---|---|---|
| 1,074,818 | 10/1913 | Sawyer | 604/257 |
| 1,655,664 | 2/1926 | Russell | 604/85 |
| 2,700,973 | 2/1955 | Ju | 128/771 |
| 2,817,372 | 12/1957 | Barr et al. | 604/411 X |
| 2,848,996 | 8/1958 | Kowal | 604/85 |
| 3,165,114 | 1/1965 | Garrett | 137/268 |
| 3,254,647 | 6/1966 | Vogel | 604/85 |
| 3,343,538 | 9/1967 | Morley | 604/122 |
| 3,612,488 | 10/1971 | Bartel et al. | 366/131 |
| 4,424,056 | 1/1984 | Urquhart et al. | 604/56 |
| 4,449,827 | 5/1984 | Karkiewicz | 366/131 |
| 4,509,861 | 4/1985 | Sjonell | 604/56 X |
| 4,534,757 | 8/1985 | Geller | 604/85 |
| 4,589,867 | 5/1986 | Israel | 604/85 |
| 4,623,334 | 11/1986 | Riddell | 604/85 |

OTHER PUBLICATIONS

Boyes et al., J. Pharm. & Exper. Thera., 74:1–8 (1970).
Foulkes, J. Pharm. & Exper. Thera., 150:406–413 (1965).

Primary Examiner—Dalton L. Truluck
Attorney, Agent, or Firm—Tilton, Fallon, Lungmus & Chestnut

[57] ABSTRACT

An intravenous drug infusion apparatus for controlling the delivery of a drug includes an in-line mixing vessel with tubular needle-like inlets which produce turbulent mixing of a drug solution contained in the vessel with an aqueous carrier. An admixed solution is discharged from the mixing vessel which provides intravenous infusion of a drug at progressively decreasing concentrations.

5 Claims, 1 Drawing Sheet

MIXER APPARATUS FOR CONTROLLING INTRAVENOUS DRUG INFUSION

GRANT REFERENCE

Experimental work relating to this invention was supported in part by grants from the United States Public Health Service: GM 15431, AG 01395, and 5M0IRR95.

RELATED APPLICATION

This application is a continuation-in-part of copending application Ser. No. 723,215, filed April 15, 1985, now U.S. Pat. No. 4,623,334 issued 11-18-86, which was a continuation-in-part of earlier Ser. No. 472,926, filed March 7, 1983, now abandoned.

FIELD OF INVENTION

The field of the invention is intravenous infusion apparatus, and more particularly the adaption of such apparatus for administering drugs.

BACKGROUND AND PRIOR ART

Intravenous solutions, such as saline or glucose solutions, are often used as carriers for the continuous administration of drugs to patients at controlled infusion rates. The drugs may be prepackaged in intravenous solution bags or bottles. The drug-containing intravenous solution may be administered by gravity flow, using a drip chamber and rate control valve, or a drop chamber with automatic rate controller. Infusion pumps may also be employed which can be preset to provide a constant solution volume delivery rate, and thereby a selected rate of the drug dissolved in the intravenous solution at a pre-established concentration.

A constant rate drug infusion apparatus, as described above, is not a clinically adequate administration means for drugs where a rapid achievement of therapeutic level is needed followed by the maintenance of a highly critical serum level to obtain therapeutic effectiveness over a longer period of administration without adverse side effects. Bolus injections of the drug can be used to provide a rapid serum concentration followed by a constant rate infusion, but the transition period between the loading injection and the achievement of a stable serum level at the desired therapeutic concentration is not effectively controlled. A rapid injection followed by a constant slow rate infusion has the disadvantage that there is a considerable time during the early hours when the plasma concentrations are subtherapeutic. A staged infusion has therefore been proposed and used to some extent, a fast constant infusion being used following the loading injection, and then by a slow constant infusion. Multiple further rapid injections may also be used to augment a slow constant infusion. All of these procedures have the disadvantages that they require attention at strictly defined times if the plasma concentration is not to rise to a toxic level or to a level giving undesired side effects, or, on the other hand, to fall to a sub-therapeutic level.

When a drug is administered intravenously the early plasma drug concentrations are much higher than the drug concentrations in tissues with a poor blood supply. With time the drug distributes to these other tissues and a steady state of distribution is reached. Once this distribution in the body has reached steady state, the aim is to maintain the steady state by infusing drug at the same rate at which it is eliminated from the body. It has been known for some time that the ideal infusion regimen to achieve and maintain constant plasma concentrations of a drug is a loading dose followed by an infusion which rails exponentially in concentration to that required to maintain a steady state. See Kruger-Thiemer (1968), *Europ. J. of Pharmacology*, 4:317. Heretofore, however, there has been no simple practice method of producing this infusion regimen.

The problem of optimized intravenous drug administration has been particularly studied in connection with the infusion of anti-arrhythmic drugs such as lidocaine. The effectiveness of lidocaine depends on the rapid achievement and maintenance of rather narrow therapeutic plasma levels, viz. 1.5 to 5.5 micrograms/milliliter. Concentrations above the critical range have been associated with toxic effects including convulsions, coma, and respiratory arrest, while lower concentrations do not adequately protect the patient against a life-threatening arrhythmia. See Salzer, et al., *Clin. Pharmacol. Ther.*, 29 (5) 617–624 (1981); and Stargel, et al., Amer. Heart J. 102 872–876 (1981). The ideal exponentially decreasing infusion between a loading injection and the constant rate infusion has been approximated by using mechanical constant rate infusion pumps and stepped decreases in the delivery rate. See Vaughn, et al. *Europ. J. Clin. Pharmacol.* 10, 433–440; and Loo, et al., *J. Pharm. Sci.* 57, 918–928 (1968).

An additional method using a mechanical mixer for achieving an exponentially decreasing delivery has been tested in dogs: Boyes, et al., *J. Pharmacol. Exp. Ther.* (1970), 174, 1–8. For a similar experimental apparatus, see Foulkes, *J. Pharmacol. Exp. Ther.* (1965) 150, 406–413. As described in these references, an intravenous solution containing no drugs is used for progressive dilution of a solution containing the drug. The solutions were mixed mechanically, viz. by a mixer or magnetic stirrer.

Boyes et al. pointed out with reference to apparatus for exponentially decreasing infusion of lidocaine that "this is probably not practical in a clinical situation." *Clinical Pharmacol. and Therap.* (1971) 12:105-116. Similarly, Tsuei et al., writing about the design of regimens to achieve and maintain a predetermined plasma drug level range, stated that: "The practical difficulties in giving an exponential intravenous infusion preclude the use of these approaches (Bolus dose with exponentially decreasing rate to constant rate) in everyday clinical situations." *Clinical Pharm. & Therap.* (1980) 28: 289–295, at 291.

SUMMARY OF INVENTION

The intravenous drug administration apparatus of this invention provides in a simple and automatic manner a first administration phase in which the drug is infused at an exponentially decreasing concentration from a high loading concentration down to a maintenance concentration, and a second phase in which there is continued delivery of the low maintenance concentration. Observation and resettings are minimized. The patient may be given one or more loading injections, such as for the administration of lidocaine as anti-arrhythmic drug, and then the infusion is started to automatically provide the exponentially decreasing phase during the transitional period while the drug is distributing from the blood into the tissues, and thereafter the maintenance concentration being adequate to replace the drug as it is eliminated from the body.

The apparatus includes a closed container with a first sterile intravenously administerable carrier containing the drug at a low patient maintenance concentration. There is also a closed rigid mixing vessel of smaller volume having a second sterile intravenously administerable carrier containing the drug at a high loading concentration. The smaller vessel functions as a mixing vessel, and is provided with inlet and outlet means constructed and arranged to provide a mixing action within the vessel. The inlet is connected to the larger volume low concentration carrier, and the outlet to the infusion cannula connected to the patient. In a preferred arrangement, hypodermic needles are employed to provide the inlets and outlets for the mixing vessel. No mechanically operated mixing device is required. The construction and arrangement of the mixing vessel inlet and outlet means providing the only mixing action associated with the vessel.

In a preferred application, the drug in the solutions of the apparatus is lidocaine. However, the apparatus is adaptable for use with many other drugs which are capable of being administered intravenously in aqueous solutions or emulsions.

In commercial embodiments of the apparatus of this invention, it is preferred to have the drug prepackaged in both the intravenous solution bag and in the mixing vessel. Further, the mixing vessel may be provided in the form of a vial equipped with a previously described inlet and outlet hypodermic needle. Closure caps may be provided for the projecting ends of the needles, which can be removed to permit their attachments to the appropriate conduits. Both the bag and the mixing vessel may be supplied as components of a complete intravenous administration set.

The mixing vessel when assembled with the intravenous infusion apparatus provides a novel means for controlling the delivery of a drug. The needles inlet and outlets provide a turbulent mixing action within the mixing vessel. The liquid supplied through the inlet needle in mixing is thoroughly mixed with the drug, and an admixed liquid is discharged through the outlet needle for patient infusion. The inner ends of the needles should terminate within the defined volume of the mixing vessel in spaced apart relation, preferably with the inner end of the inlet needle terminating in the lower portion of the vessel and the inner end of the outlet needle terminating in the upper portion of the vessel.

THE DRAWING

The apparatus of this invention is shown in an illustrative embodiment in FIG. 1 of the attached drawing. It should be understood that certain of the components of the apparatus are shown diagrammatically because of their well-known construction, and that the relative size of the apparatus components, such as the solution bag and the mixing vessel, can be varied widely and are not necessarily shown to scale in the drawing.

DETAILED DESCRIPTION

Figure 1:
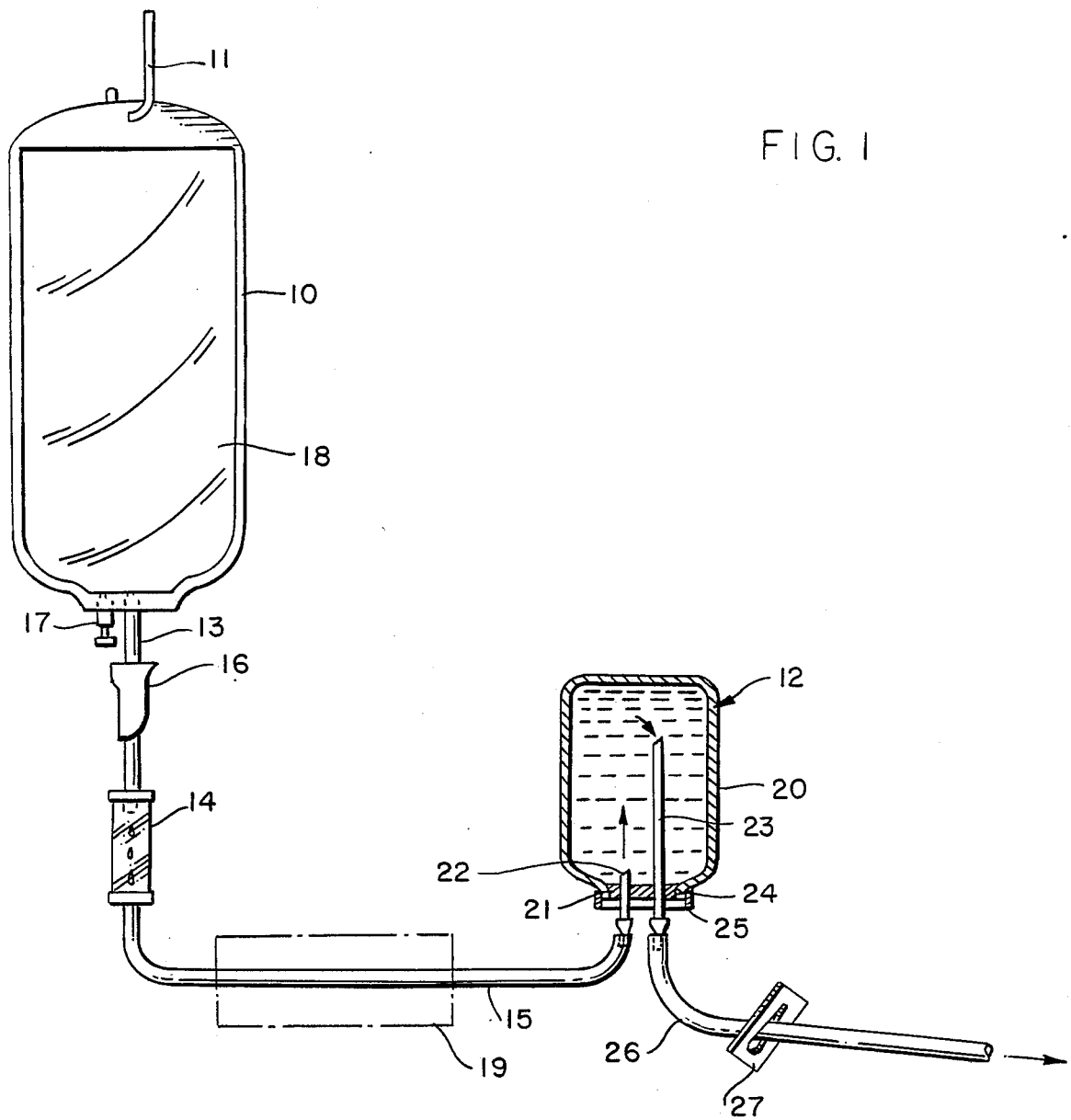

The intravenous drug administration apparatus of this invention utilizes as one of its components a closed container with a first sterile intravenously administerable aqueous solution therein. This container may be a standard intravenous solution bag or bottle containing 0.5 or 1.0 liters of an intravenous solution, such as a normal saline solution, a glucose solution, etc.

The drug to be administered is incorporated in the intravenous solution at a low maintenance concentration. For example, the drug may be lidocaine dissolved in the amount of 2,000 mg in 1,000 ml of normal saline, giving a concentration of 2 mg/ml. Other anti-arrhythmic drugs such as mexiletine, disopyramide, bretylium, flecainide, and procainamide can be administered. Drugs for other conditions can be advantageously infused in the same manner. For example, the apparatus may be used for the administration of hyponotic anaesthetic agents such as methohexitone, disoprofol, or midazolam; an analgesic agent such as alfentanyl; a respiratory stimulant such as doxapram; a drug for premature labor such as ritodrine or salbutamol; and drugs for acute asthmatic attacks such as aminophylline, salbutamol and terbutaline.

The large volume container providing a solution of the drug at the low maintenance concentration will have an outlet positionable at the bottom thereof for gravity outflow, as is well known with respect to intravenous solution bags and bottles. The container may also be provided with an inlet port for introduction of the drug, or the drug may be prepackaged in the container.

The apparatus also includes a closed mixing vessel of smaller volume having a second sterile intravenously administerable aqueous carrier providing a high loading concentration of the drug. The mixing vessel provides a defined volume. Preferably this defined volume has an upward extent, including a lower portion for receiving the diluting liquid from the large volume container and a spaced upper portion for discharging of an admixed liquid.

The intravenous carrier may be the same as that in the larger volume container, that is, it will be a saline solution, a glucose solution, etc., and the same drug can be dissolved or emulsified in the second solution, but at a considerably higher concentration. This higher concentration will correspond with the desired high loading concentration of the drug for an initial infusion. For example, where the drug is lidocaine and a normal saline solution is used, the mixing vessel and the solution therein may have a volume of 20 ml and may contain 200 mg lidocaine, giving a concentration of 10 mg/ml. As stated above, the larger volume container may have a lidocaine concentration of about 2 mg/ml. It will be understood that the relative concentrations and relative volumes of the first and second solutions are subject to wide variations, depending on the particular drug being administered, and the desired length of the period of administration. However, in general, the loading concentration in the second solution will be at least two to three times that of the maintenance concentration in the first solution, and the volume of the first solution will be at least five times that of the second solution.

The mixing vessel is provided with an inlet connected to the container outlet by conduit means, and the inlet means is designed to provide a solution mixing action within the vessel. The vessel is also provided with outlet means positioned and arranged with respect to the inlet means so that mixing of the solutions can occur within the vessel for discharging an admixed solution to the outlet. A delivery conduit is connected to the outlet for intravenous delivery of the admixed progressively diluted solution to a patient during a first phase of the administration. In the second phase, with the continued administration of the maintenance solution no mixing dilution is needed. The concentration of the drug in the solution of the mixing vessel is at the same level as that of the larger volume container.

If the mixing vessel initially contains the drug in the form of a water-soluble powder, the initial flow of liquid from the large volume container will fill the mixing vessel and begin to solubilize the drug, thereby in a short time providing a solution of the drug within the mixing chamber.

The apparatus can be operated entirely by gravity flow. The container with the low concentration drug is positioned at a higher level than the mixing vessel, and the solution is permitted to flow therefrom and into the mixing vessel under the action of gravity. However, it may be desirable to employ a constant rate pump. The pump may be preset to a desired flow rate, and interposed between the container and the mixing vessel. The low concentration solution is delivered from the outlet side of the pump to the mixing vessel. Suitable pumps are commercially available.

Other standard components of intravenous administration sets will preferably be included. For example, a drip chamber and a rate control clamp, such as a roller clamp, may be used in the conventional manner. Other commonly employed devices can be used, such as automatic rate controllers, to assure the maintenance of a constant drip rate. There can also usually be provided a shut-off clamp on the downstream conduit between the mixing vessel and the cannula attached to the patient.

A representative assembly of the components referred to above, including those especially adapted for performing the method of the present invention, are shown in the accompanying drawing. FIG. 1 is shown in somewhat diagrammatic form and it should be understood that the components are not to exact scale. The intravenous solution bag, as shown, which contains the low concentration solution of the drug, is provided with a hanger for mounting it at a level above the mixing vessel to provide for gravity flow between the solution bag and the mixing vessel. In the illustration given, the bag has a lower outlet tube connecting to a drip chamber, which in turn is connected to the inlet of the mixing vessel by a conduit. A roller clamp may be used to provide for the drip rate adjustment. The lower end of the solution bag is also provided with an access port tube through which a drug may be introduced into the intravenous solution within the bag. Preferably, however, the drug is prepackaged, in which case an access port will not be needed.

As shown in FIG. 1, a conventional drip chamber is provided below the intravenous solution bag and connected by a conduit to the mixing vessel. The roller clamp may be mounted on the conduit adjacent the drip chamber for adjusting the drip rate, and thereby predetermining the constant flow rate. Alternatively, as described above, an automatic controller can be used. Further, as indicated by the dotted lines, a constant rate pump may be interposed in the conduit for passing the solution into the mixing vessel at a constant preset rate.

The mixing vessel will contain the sterile aqueous solution of the drug at a high concentration corresponding to the desired loading concentration. In the illustration given, the mixing vessel consists of a small bottle or vial, having a rubber closure plug through which extend two hollow needles, a short inlet needle and a long outlet needle. The plug with the needles frictionally held therein is secured in the neck of the vial by means of a metal clamping ring. The needles may comprise commercially available standard hypodermic needles, or special mixing needles may be designed for this application. The inlet needle, as shown, terminates in the lower portion of the mixing vessel, while the outlet needle extends into and receives solution from the upper portion of the vessel. With this arrangement, mixing action occurs within the vessel. The solution introduced through the inlet needle enters as a jetstream to provide mixing and turbulence within the vessel. Since the ends of the inlet and outlet needles are separated, mixing can occur within the vessel, so that an admixed solution is discharged through the outlet needle. The outer end of the outlet needle is connected to a conduit for delivery to the venous cannula of the patient. As shown, a slide clamp is mounted on the outlet conduit, which may be moved from an open position to a clamping position cutting off the flow.

The mixing vessel, such as the one shown in FIG. 1, may be of relatively rigid construction, for example, it may be formed of glass or a plastic to provide a defined volume. It is also important to employ a needle like inlet tube to promote turbulent mixing within the vessel. Another important feature is the physical separation between the points of fluid introduction and removal, that is, ends of the inlet and outlet tubes should be spaced apart within the mixing vessel. While it is advantageous to use a hypodermic needle to form the outlet, the outlet is less critical than the inlet and the spacing of the outlet from the inlet. With these features, low pressures and low flow rates can be employed to provide continuous administration of the drug for several hours.

With the apparatus as shown in FIG. 1, after the patient has been given one or more injections of the drug to produce immediate loading, the slide clamp may be opened to permit the beginning of the infusion. At the start of the infusion, the drug will be administered at the high concentration of the mixing vessel. As the administration proceeds, the low concentration solution from the bag will progressively mix with and dilute the solution in the mixing vessel, thereby providing a close approximation to an exponentially reducing concentration as delivered to the patient. Since the volume of solution in the bag is much greater than that in the mixing vessel, a condition will be reached at which there is remaining solution in the bag, while the concentration of the solution in the mixing vessel is the same as that of the bag. Thereafter, the continued administration will be at the low maintenance concentration of the bag solution. During all phases of the administration, there will be a minimal need to monitor or attend the administration apparatus.

In an illustrative embodiment, a one liter intravenous solution bag containing 0.9% saline can be used. 10 ml lidocaine HCL (200 mg/ml) is introduced into the bag by an additive syringe, resulting in a lidocaine HCL concentration of 2 mg/ml (1.7 mg/ml lidocaine). The mixing vessel can consist of a 20 ml vial or prepackaged lidocaine solution containing 200 mg lidocaine HCL (8.7 mg/ml lidocaine). The vial may have a rubber closure through which hypodermic needles are inserted. The vial closure is pierced with two needles, the needle providing the inlet being $\frac{1}{2}''\times 27$ SWG hypodermic needle, and the outlet being provided by a $1\frac{1}{2}''\times 22$ SWG hypodermic needle. The inlet needle terminates in the lower portion of the inverted container, and the outlet needle extends into the upper portion, in the manner illustrated in FIG. 1. Preferably, although not essentially, the mixing vessel is completely full of solution, thereby eliminating any air space which might create air bubbles in the infusion solution.

In use of the apparatus, total delivery time will depend on the volume of the low concentration solution. For example, with a 1 liter volume and a flow rate of 1 ml/min infusion can run for approximately 16.7 hours. At the same rate with a low concentration solution volume of 0.5 liters, the infusion can be contained for approximately 8.3 hours.

I claim:

1. An intravenous drug infusion apparatus for controlling the delivery of a drug, comprising a container with an intravenously administrable aqueous carrier therein for discharge through an outlet thereof, a mixing vessel providing a defined interior volume for containing a solution of the drug to be infused, said defined volume providing upper and lower portions in spaced apart relation, a hollow inlet needle having an inner end extending into and terminating in said defined volume lower portion, conduit means connected to the outer end of said inlet needle providing communication between said inlet needle and said container outlet for transfer of the aqueous carrier into said mixing vessel, a hollow outlet needle having an inner end extending into and communicating with said defined volume upper portion, and delivery conduit means connected to the outer end of said outlet needle for infusion of said drug, said inlet and outlet needles being dimensioned and arranged to provide a turbulent mixing of the drug within said vessel with the incoming liquid so that admixed liquid is discharged through the outlet needle to the delivery conduit means.

2. The infusion apparatus of claim 1 in which said mixing vessel is provided with a pierceable closure and said inlet and outlet needles extending through said closure, said outlet needle being longer than said inlet needle.

3. Intravenous drug infusion apparatus for controlling the delivery of a drug, comprising a container with an intravenously administerable aqueous carrier therein for discharge through an outlet thereof, a mixing vessel providing a defined interior volume smaller than that of said container and aqueous carrier, a solution of the drug to be infused contained in said mixing vessel, said defined volume providing upper and lower portions in vertically spaced apart relation, tubular inlet means extending into and communicating with said defined volume lower portion, conduit means providing fluid communication between said inlet means and said container outlet for transfer of the aqueous carrier into said mixing vessel, tubular outlet means extending into and communicating with said defined volume upper portion, and delivery conduit means in fluid communication with said mixing vessel outlet means for infusion of said drug, said mixing vessel inlet and outlet means being constructed and arranged to providing turbulent mixing within said vessel of said drug solution and the incoming aqueous carrier so that a continuously admixed solution is discharged to the delivery conduit means, whereby a progressively decreasing concentration of said drug can be infused.

4. The intravenous drug infusion apparatus of claim 3 in which said mixing vessel inlet means comprises a hollow needle having its inner end extending into said defined volume lower portion, and said mixing vessel outlet means comprises a hollow needle having its inner end extending into said defined volume upper portion.

5. The intravenous drug infusion apparatus of claim 4 in which said inlet and outlet needles are hypodermic needles.

* * * * *

UNITED STATES PATENT AND TRADEMARK OFFICE
CERTIFICATE OF CORRECTION

PATENT NO. : 4,820,269

DATED : April 11, 1989

INVENTOR(S) : James G. Riddell

It is certified that error appears in the above-identified patent and that said Letters Patent is hereby corrected as shown below:

Claim 3, line 21, cancel "providing" and substitute -- provide --.

Signed and Sealed this

Twenty-eighth Day of November 1989

Attest:

JEFFREY M. SAMUELS

Attesting Officer     Acting Commissioner of Patents and Trademarks